United States Patent
Dubrul et al.

(10) Patent No.: US 6,635,068 B1
(45) Date of Patent: Oct. 21, 2003

(54) OCCLUSION, ANCHORING, TENSIONING AND FLOW DIRECTION APPARATUS AND METHODS FOR USE

(75) Inventors: William Richard Dubrul, Redwood City, CA (US); Richard E Fulton, Grand Junction, CO (US)

(73) Assignee: Artemis Medical, Inc., San Mateo, CA (US)

(*) Notice: Subject to any disclaimer, the term of this patent is extended or adjusted under 35 U.S.C. 154(b) by 0 days.

(21) Appl. No.: 09/248,083

(22) Filed: Feb. 9, 1999

Related U.S. Application Data (60) Provisional application No. 60/104,922, filed on Oct. 20, 1998, provisional application No. 60/077,281, filed on Mar. 9, 1998, and provisional application No. 60/074,183, filed on Feb. 10, 1998.

(51) Int. Cl.⁷ ............................................. A61M 29/00
(52) U.S. Cl. ...................................................... 606/200
(58) Field of Search .............................. 606/191, 151, 606/198, 200; 623/1, 1.2; 604/194

(56) References Cited

U.S. PATENT DOCUMENTS

| | | | | |
|---|---|---|---|---|
| 2,816,552 A | | 12/1957 | Hoffman | 128/305 |
| 3,320,957 A | | 5/1967 | Sokolik | 128/311 |
| 3,834,394 A | * | 9/1974 | Hunter et al. | 606/191 |
| 3,996,938 A | | 12/1976 | Clark, III | 128/348 |
| 4,425,908 A | * | 1/1984 | Simon | 128/899 |
| 4,572,186 A | * | 2/1986 | Gould et al. | 604/104 |
| 4,611,594 A | | 9/1986 | Grayhack et al. | 128/328 |
| 4,619,246 A | * | 10/1986 | Molgaard-Nielsen et al. | 606/200 |
| 4,650,466 A | | 3/1987 | Luther | 604/95 |
| 4,799,495 A | | 1/1989 | Hawkins et al. | 128/754 |
| 4,852,568 A | | 8/1989 | Kensey | 128/325 |
| 4,895,560 A | | 1/1990 | Papantonakos | 604/22 |
| 4,921,484 A | | 5/1990 | Hillstead | 604/104 |
| 4,966,583 A | | 10/1990 | Debbas | 604/98 |
| 4,986,279 A | | 1/1991 | O'Neill | 128/754 |
| 4,994,069 A | * | 2/1991 | Ritchart et al. | 606/191 |
| 5,030,201 A | | 7/1991 | Palestrant | 604/22 |
| 5,031,634 A | | 7/1991 | Simon | 128/754 |
| 5,059,197 A | | 10/1991 | Urie et al. | 606/116 |
| 5,100,423 A | | 3/1992 | Fearnot | 606/159 |
| 5,102,415 A | | 4/1992 | Guenther et al. | 606/159 |
| 5,158,565 A | | 10/1992 | Marcadis et al. | 606/185 |
| 5,183,463 A | | 2/1993 | Debbas | 604/98 |
| 5,192,290 A | | 3/1993 | Hilal | 606/159 |
| 5,195,533 A | | 3/1993 | Chin et al. | 128/754 |
| 5,211,658 A | * | 5/1993 | Clouse | 623/1 |

(List continued on next page.)

FOREIGN PATENT DOCUMENTS

| | | | | |
|---|---|---|---|---|
| DE | 39 13935 | | 4/1989 | |
| DE | 9205797-7 | * | 7/1992 | 606/200 |
| GB | 2020557 | | 11/1979 | |
| WO | WO 95/02370 | | 1/1995 | |
| WO | WO 97/20504 | | 6/1997 | |
| WO | WO 98/08441 | | 3/1998 | |
| WO | WO 99/04704 | | 2/1999 | |
| WO | WO 99/44506 | | 9/1999 | |

*Primary Examiner*—Kevin T. Truong
*Assistant Examiner*—(Jackie) Tan-Ugen T. Ho
(74) *Attorney, Agent, or Firm*—James F. Hann; Haynes Beffel & Wolfeld LLP (57) ABSTRACT

Wires, catheters, endoscopes, etc. and their methods that have flow directed distal ends, which allow and facilitate management of these devices during use are disclosed. Additionally instant invention allows for distal anchoring so that the device will remain in a location once it has arrived and its method for use. Further, the instant invention describes an apparatus and method for a tensioning characteristic to be applied along the device once it is place that will facilitate the passing of another member along the initially placed member. Last, a novel occluder is disclosed and its method of use.

33 Claims, 4 Drawing Sheets

U.S. PATENT DOCUMENTS

| | | | |
|---|---|---|---|
| 5,221,269 A | 6/1993 | Miller et al. | 604/281 |
| 5,336,191 A | 8/1994 | Davis et al. | 604/165 |
| 5,365,943 A | 11/1994 | Jansen | 128/772 |
| 5,370,660 A | 12/1994 | Weinstein | |
| 5,382,259 A * | 1/1995 | Phelps et al. | 606/191 |
| 5,383,892 A | 1/1995 | Cardon et al. | 606/198 |
| 5,396,897 A | 3/1995 | Jain et al. | 128/748 |
| 5,466,225 A | 11/1995 | Davis et al. | 604/165 |
| 5,507,769 A | 4/1996 | Marin et al. | 606/198 |
| 5,527,276 A | 6/1996 | Bruce | 604/54 |
| 5,562,725 A | 10/1996 | Schmitt et al. | 623/1 |
| 5,571,091 A | 11/1996 | Davis et al. | 604/165 |
| 5,595,185 A | 1/1997 | Erlich | 128/754 |
| 5,601,595 A * | 2/1997 | Smith | 606/200 |
| 5,603,722 A | 2/1997 | Phan et al. | 606/198 |
| 5,643,282 A | 7/1997 | Kieturakis | 606/114 |
| 5,665,092 A | 9/1997 | Mangiardi et al. | 606/86 |
| 5,720,764 A | 2/1998 | Naderlinger | 606/200 |
| 5,728,133 A | 3/1998 | Kontos | 606/213 |
| 5,746,767 A * | 5/1998 | Smith | 606/200 |
| 5,749,883 A | 5/1998 | Halpern | 606/159 |
| 5,766,203 A | 6/1998 | Imran et al. | 606/198 |
| 5,769,816 A | 6/1998 | Barbut et al. | 604/96 |
| 5,782,860 A | 7/1998 | Epstein | |
| 5,792,157 A | 8/1998 | Mische et al. | 606/159 |
| 5,795,308 A | 8/1998 | Russin | 600/567 |
| 5,800,409 A | 9/1998 | Bruce | 604/280 |
| 5,800,445 A | 9/1998 | Ratcliff et al. | 606/116 |
| 5,810,744 A | 9/1998 | Chu et al. | 600/567 |
| 5,810,849 A | 9/1998 | Kontos | 606/144 |
| 5,814,064 A | 9/1998 | Daniel et al. | 606/200 |
| 5,827,312 A | 10/1998 | Brown et al. | 606/167 |
| 5,827,324 A | 10/1998 | Cassell et al. | 606/200 |
| 5,855,585 A | 1/1999 | Kontos | 606/144 |
| 5,868,708 A | 2/1999 | Hart et al. | 604/104 |
| 5,876,411 A | 3/1999 | Kontos | 606/144 |
| 5,879,357 A | 3/1999 | Heaton et al. | 606/116 |
| 5,916,145 A | 6/1999 | Chu et al. | 600/121 |
| 5,925,060 A * | 7/1999 | Forber | 606/191 |
| 5,928,260 A | 7/1999 | Chin et al. | 606/200 |
| 5,928,261 A | 7/1999 | Ruiz | 606/200 |
| 5,984,947 A * | 11/1999 | Smith | 606/200 |
| 6,027,520 A | 2/2000 | Tsugita et al. | 606/200 |
| 6,053,876 A | 4/2000 | Fisher | |
| 6,168,622 B1 * | 1/2001 | Mazocchi | 623/1 |
| 6,179,860 B1 * | 1/2001 | Fulton, III et al. | 606/200 |
| 6,221,086 B1 * | 4/2001 | Forber | 606/151 |
| 6,331,166 B1 | 12/2001 | Burbank et al. | |

* cited by examiner

OCCLUSION, ANCHORING, TENSIONING AND FLOW DIRECTION APPARATUS AND METHODS FOR USE

CROSS REFERENCE TO RELATED APPLICATIONS

The present invention is a continuation of provisional patent application Ser. No. 60/074,183 filed on and claiming priority of Feb. 10, 1998, the full disclosure of which is incorporated herein by reference, provisional patent application Ser. No. 60/077,281 filed on and claiming priority Mar. 9, 1998, the full disclosure of which is incorporated herein by reference and provisional patent application Ser. No. 60/104,922 filed on and claiming priority Oct. 20, 1998, the full disclosure of which is incorporated herein by reference.

1. Field of the Invention

The present invention relates to medical devices and methods. In particular, the present idea relates to improved guide wires or catheters and method for their use, where the devices have a distal mechanism that acts as a mechanism for: 1. Flow Directed, using the natural flowing fluids, pressure differentials or contractile forces of the body onto the distal mechanism to direct its motion and direction or 2. Anchored, so that once the device is in the desired location, it can be anchored against the tissue where it rests; 3. Tensioned, so that placement of a device, over the guide wire is accomplished with less difficulty and 4. Occluded, so that vessels and aneurysms can be occluded.

BACKGROUND OF THE INVENTION

Guide wire management in the operating room is problematic, and threading the needle of the arteries or other vessels including, but not limited to veins, intestines, fallopian tubes, etc. to reach the area to be treated is difficult. Further, once the guide is in the desired location, it is often difficult to make certain that the it remains in that location. Even further, once the guide wire, catheter, endoscope or other device is in the desired location and another device is placed over, through or along side it, the initially placed device has a tendency to move due to the forces exerted on it when other devices are using it as a guide.

Additionally, other anchors are required for attaching tissue or other matter to improved or different locations within the body.

Even further, vessel occluders are often required for a variety of medical procedures.

The instant invention describes a device that facilitates all of these procedures in a novel fashion.

For these reasons, it is desirable to provide an improved devices and methods for their use, which facilitate 1. using the physiologic motions of the body to help direct the device. In addition, flow pressure differential can be artificially created or enhanced by the technician/physician so that this same technology can be used when physiologic means is unavailable or insufficient. Further, the natural contractile forces of the body (e.g. those of the intestinal tract, gall bladder, esophagus, etc.) can be harnessed so that the device including, but not limited to guide wires, catheters, endoscopes, etc. are moved along with those forces. 2. Even further, it is desirable to provide a device that has an anchoring mechanism on it so that it will not move once in its desired position. 3. And yet even another desired characteristic would be to provide an anchored device that has a tensioning characteristic applied to it for placement of other devices over through or along side the first placed device. 4. And finally, another desired characteristic is that of a simple and effective occlusion system.

There is a continuing need for improved devices to meet at least the following objectives.

The first objective is to reduce cost. This is particularly important in recent years where it is clear for safety and sanitary reasons that these will be single use devices. A device, although it performs a function in some improved manner, will not be widely used if it is considerably more costly than the alternatives available.

A second objective is to provide a device that is simple to use and in a very real sense simple to understand. This will encourage its adoption and use by medical personnel. It will also tend to keep cost low.

The third objective is to provide a device that entails a procedure with which the medical profession is familiar so that the skills that have been learned from previous experience will continue to have applicability.

A fourth objective relates to the effectiveness and thoroughness with which the device is intended.

A fifth objective concerns safety; a matter which is often so critical as to trump the other considerations. It is important to avoid unnecessary tissue trauma.

There are trade-offs in design considerations to achieve the above five interrelated objectives. Extreme simplicity and a very simple procedure might over compromise safety. Addressing all of these considerations calls for some trade-off between the objectives.

Accordingly, a major object of this invention is to provide an improved occlusion, tensioning, anchoring and flow device that achieves the objectives of reduced cost, enhanced simplicity, a standard procedure, high effectiveness and a high degree of safety. Most particularly, it is an object of this invention to achieve these objectives with an enhanced trade-off value for the combined objectives.

For these reasons, it is desirable to provide an improved device that may circumvent some of the problems associated with previous techniques. This improved medical device provides a new configuration that will eliminate some of those problems and methods for their use, which facilitate removal of vascular obstructions in the operating room or interventional suite.

BRIEF DESCRIPTION

In brief, one embodiment of this invention is particularly adapted to the anchoring of wires or tubes within the tubular channels of the body including, but not limited to veins, arteries, intestines, nasal passages, ear canal, etc. Further, this anchoring embodiment has a applicability in applying an anchor to tissues or other matter to areas of the body other than in tubular channels including, but not limited to the face, breast joints, etc. This embodiment has a support wire with an engaging element.

The support wire is a dual element support wire having a core and an annular shell that slides on the core. The distal end of the core is attached to the distal end of the annular braided element and the distal end of the shell is attached to the proximal end of the annular braided element. Thus movement of the core and shell relative to one another moves the braided element from a radially retracted position which is useful for insertion into the body to a radially expanded position which expands it to the sidewall of the tubular channel or against other tissue or matter within the body. When the annular braided element is in its radially compressed (smaller diameter) state, it can be passed through or around occlusions together with the rest of the wire to reside on the distal end of the occlusion in the case of tubular channels with occlusions. It is a preferred embodiment of the instant invention that it can be made very small. When the braided element is expanded and pulled proximally (that is, in a retrograde fashion), it will engage the walls of the tubular channel and the elongate support wire can be put into tension. This distal engaging tubular braid element may or may not be covered by or integrated with a thin film or membrane to create patency or other desirable characteristics.

The instant invention also describes another use of the same device of the instant invention with minor changes. In this case, the tubular braid distal expansile mechanism may be used on the end of a guide wire or catheter so that once deployed in a tubular channel with flow such as arteries and veins, the expanded mechanism can carry the support wire in the direction of the flow. In order to accomplish this flow characteristic of the instant invention, it may be desirable to deploy the distal expanding tubular braid whereby the support wire becomes 'floppy' in nature so that it will flow with the expanded 'umbrella'. The author uses the phrase 'umbrella' only as a communication tool in that an umbrella starts out with a small diameter shaft in its un-deployed condition (radially compressed condition) and ends up with a large diameter configuration when deployed. The shape of the expanding mechanism is varied and includes, but is not limited to an umbrella shape, a spheroid shape, an ovoid shape, a conical shape, a disc-shape, etc. The inventors have fabricated at least all of the aforementioned shapes using tubular/annular braid and successfully tested the flow, anchoring, tensioning and occlusion characteristics in both a static and dynamic in vitro environment. Creating the expanded annular braided mechanism is accomplished by pulling the inner wire of the support wire out of the outer tube. The outer tube can be made of very flexible material so that the inner wire gives the structure all of the support. When the 'umbrella reaches the desired location which is usually determined by image intensification including, but not limited to x-ray, ultrasound, MRI, etc., the inner wire can be re-inserted into the flexible outer tube of the support wire to give the desired support required. Also once the 'umbrella' with the flexible outer tube needs to be removed, the inner wire can be an actuator to un-deploy the expanded braided element back to its smaller and radially compressed size. This is accomplished by bonding the outer tube of the support wire to the distal end of the tubular braid expanding element and the inner wire of the support wire is slightly bonded to the distal end of the braided expanding element. This slight bond could also be an interference fit where the inner wire snaps into and out of the distal end of the braided expanding element.

Even further, by making another minor change to the instant invention would be to use the braided expanding element as a permanent or temporary occluder without the support wire being left in place. This is accomplished by having the outer tube not bonded to the proximal end of the expanding element and the inner wire of the support wire to be only slightly bonded to the distal end of the expanding braided element. In this case, the inner wire is pulled in a retrograde direction relative to the outer tube. This action causes the expanding braided element to expand radially. Once the expanding element expands to the desired shape for the particular application and occlusion, the inner wire is pulled out of the 'snap' or interference fit on the distal end of the expanding braided element and the expanded braid occluder is left in place when both the inner and outer member of the support wire is removed from the body.

Hence, nearly the same invention allows the use for four different applications in the health care field.

SUMMARY OF THE INVENTION

The instant invention provides an improved device of the type having a shaft with a proximal end and a distal end. The improvement comprises configuring at least a distal portion of the shaft so that it can assume a shape(s) along its shaft (proximally, mid-section or distally) that will act as an 'umbrella' type configuration. In the case of body channels or cavities, this expanded mechanism(s) is moved along the lumen (artery, vein, intestine, stent, graft, or other hollow vessel or organ) until it is in the desired location and is then deployed. For using the instant invention as a flow directed device, the expanding element is deployed when in position to be carried with the flow in the channel. Once the device is in the desired location, the user (physician/technician) can actuate the expanding mechanism(s) so that it is enlarged beyond its original size/diameter and aid in carrying the support wire, anchoring the wire, tensioning the wire or causing occlusion. MIS (Minimally Invasive Surgery) or LIS (Least Invasive Surgery) devices described herein such as catheters and guide wires, for example are the most common tools used by least invasive interventionalists today. These devices are available in a variety of shapes and sizes from 0.008–500" diameters and from 6.0–80.0" in length. In other respects, the catheters and guide wires or other device(s) of the instant invention will have the geometries, characteristics, and dimensions of those commonly employed for the intended purpose (e.g. introduction to a blood vessel (LIS) or surgical tissue anchoring or occlusion (MIS). MIS and LIS are often interchanged in their usage. Usually LIS refers to catheters, guide wires, (and the like) that are used within the body, often within the channels of the body. MIS typically refers to videoscopic surgery where miniature cameras are used to accomplish surgery. However, because of the large crossover of the use of these terms, the inventors do not wish to limit the scope of the devices described herein when these terms are used.

Further, the instant invention provides for an anchor located along its shaft (usually at its distal portion). This anchor allows the device to maintain the desired position once it is in the desired location.

Even further, the anchor of the instant invention allows a tension to be applied to the so that another structure can be more easily placed with the first device. Alternatively this tension may not be required, but just the anchor so that an another member can be advanced with the help of the first member and without loosing the preferred location.

Guide wires are the most common tools used by least invasive interventionalists today. These guide wires are available in a variety of shapes and sizes from 0.008–0.045" diameters and from 6.0–80.0" in length. In other respects, the guide wires of the present idea will have the geometries, characteristics, and dimensions of those commonly employed for the intended purpose, e.g. introduction to a blood vessel. Typically, for vascular applications, the flexible core will have a length in the range from 10 cm to 300 cm diameter and in the range from 0.1 mm to 1 mm.

Additionally there are a variety of configurations such as floppy, J-Tip, stiff, Moveable Core, Nitinol, Stainless Steel, Polymer Coated, Lubricious Coated, just to name a few. The instant invention can be used with any of the existing guide wires that are commercially available today and that may become commercially available in the future. As stated above the characteristic design of the instant invention is that at least a portion of the distal end of the wire (or other device) has some mechanism that allows physiological forces (or other artificially created forces) in the lumens of the body to carry the guide wire to a desired location or that the distal shape mechanism allows for anchoring or that the distal shape allows for tension to be applied to the wire, catheter or other device or that the distal expanded braided element is used as an occluder.

2. Description of the Background Art

Pertinent descriptions are set forth in a number of issued U.S. patents, including U.S. Pat. Nos. 5,275,611, 5,312,360, 4,696,304, 5,176,659, 5,437,631, 5,606,979, 5,779,672, 5,456,667, 5,733,294 and 5,209,727. A pin vise for helping grip the proximal end of a guide wire is illustrated in U.S. Pat. No. 4,858,810. U.S. Pat. Nos. 5,275,611, 5,312,360 describe a tension guide and dilator. U.S. Pat. No. 5,779,672 describes a detachable inflatable occlusion balloon. U.S. Pat. No. 5,456,667 describes a temporary stent on a catheter. U.S. Pat. No. 5,733,294 describes a self-expanding cardio-vascular occlusion device. U.S. Pat. Nos. 5,437,631, 5,591,204 and 5,383,897 describe a puncture wound sealer. U.S. Pat. No. 5,626,614 describes a tissue anchor for anchoring the stomach to the abdominal wall. U.S. Pat. No. 4,372,293 describes an instrument for the surgical correction of ptotic breasts. U.S. Pat. Nos. 5,730,733 and 5,336,205 describe flow-assisted catheters.

BRIEF DESCRIPTION OF THE DRAWINGS

FIG. 1-A is an illustration of the expandable guide wire or catheter in its relaxed un-deployed state (normally closed). FIG. 1-B is a schematic illustration of the expandable guide wire or catheter in its expanded state. FIG. 1-C is a schematic illustration of the 'detached' occluder.

FIG. 4-A is a schematic illustration of the detached occluder in place in a tubular channel within the body. FIG. 4-B is a schematic illustration of the occluder being advanced in a tubular channel toward an aneurysm. FIG. 4-C is a schematic illustration of the detached occluder in place in the aneurysm.

Although FIGS. 3 & 4 indicate use of the instant invention in a tubular channel of the body, it is recognized and disclosed heretofore that the instant invention has applicability toward many other areas other than those in the figures including, but not limited to anchoring the intestines or stomach, anchoring hearing aids, occlusion of any hollow structure, anchoring the bladder, anchoring the breasts to create a lifting force, anchoring the facial tissues to lift those tissues, etc. Further, although the instant invention in FIG. 1-B illustrates a relative motion of the inner and outer elongate member, it is recognized and disclosed heretofore that the expanding mechanism may be deployed any number of ways including, but not limited to self expansion (permanent set in the expanding mechanism that is constrained by an outer tubular channel prior to deployment, magnetic means, thermal gradient mechanisms, electrical stimulation, etc.

DESCRIPTION OF THE EXEMPLARY EMBODIMENTS

Although the instant invention relates to four basic embodiments, those being flow directed, anchoring, tensioning and occluding, the instant invention is submitted for prosecution because the four embodiments are so closely related. Further and equally important is that the mechanical configuration(s) for all four embodiments of the present invention are similar.

The device of the instant invention is used for intervention into the tubular channels (lumens) of the body including, but not limited to arteries, veins, biliary tract, urological tract, intestines, nasal passages, ear canals, etc. Further, it can be useful as a suturing anchor in places of the body including, but not limited to adhering the stomach or other intestine to the abdominal wall in the case of feeding gastrostomies, jejunostomies, etc. Other anchoring applications of the instant invention include MIS facelifts and the repair of ptotic breasts. Even further, the instant invention is used for the repair of aneurysms of other permanent vessel occlusions. Such other permanent vessel occlusions would have applicability for occlusion of tributaries of vessels for vessel harvesting. The instant invention is particularly convenient to use in an operating room, interventional suite, patients' bedside, in an emergency room environment or in any emergency situation. One preferred embodiment of the instant invention is that it is inserted into the tubular channel of the body to utilize the flow directed characteristics of the invention. Once the device is in a flow/differential pressure situation, the inner core, mandrel/wire/string/member is deployed (usually pulled by the physician outside the body) so that the umbrella/trap configuration on the distal portion of the device opens. At the same time, the distal portion of the device becomes 'floppy' in nature so that it will follow the tortuous paths of the lumen without causing deleterious complications normally realized with conventional guide wires where they inadvertently damage the inner wall of the vessel when trying to cross said tortuous paths. The device is then carried in the direction of flow or of lower pressure (or with any contractile forces that may exist).

Once the device is in the desired position within the body, the umbrella like mechanism may or may not be un-deployed. In this case, once the device is removed from the package and before insertion into the body, the mechanism on the distal portion of the guide wire may be unopened (normally closed).

Alternatively, the device could have a distal configuration that causes it be moved in the direction of flow or in the direction of less pressure (or with the contractile forces) at the time it is opened from the package (e.g. normally opened). In this case the device is placed in the motion situation in the tubular channel of the body and is carried to the desired location. In the normally open position, the device may be very floppy in nature so that it will easily travel through the lumen of the body due to the pressure differential/flow/contractile forces. Once in position, the mechanism at the distal portion of the device may or may not be closed by some other mechanical means by the technician outside the body. One way of undeploying the distal 'umbrella' mechanism is by re-inserting the inner core so that the expanded mechanism becomes small or in its radially compressed state. Another advantage of re-inserting the inner core wire into the outer 'floppy' tube would be to make the support wire somewhat stiff, facilitating the insertion of another device over, through or along side the support wire that is attached to the expandable mechanism. Further, the umbrella like mechanism could become enlarged so that it will anchor in the lumen to keep its desired position.

Possible configurations of the distal mechanism are varied. One such mechanism is a balloon that is inflated for flow and deflated when not required. Another configuration that could be used is a mechanism known as a malecot. This malecot is a common configuration used in catheters for holding them in place (in the case of feeding tubes in the intestines). It is usually a polymeric tube that has four slits diametrically opposed. When the distal tip of the malecot is put into compression (usually by pulling an inner wire or member), the four sides of the polymer are pushed outward so as to create a larger diameter on the distal tip. Alternatively, the normal configuration of the malecot could be an open configuration whereby, when put into tension (large or small), the malecot closes to come near to or equal to the diameter of the elongated member. This larger diameter is larger than the body length of the catheter or wire. Another alternative is one that is similar to the malecot, but uses a multi-stranded braid on the distal end. When the braid is put into compression, the braid is pulled together and it flares out to create a larger diameter only the distal end. Alternatively either the braid or the malecot can have a permanent set put into in so that it is normally open or of the larger diameter. In this case, when it is put into tension (usually from some inner core wire or mandrel) it collapses down to the diameter of the body of the wire or catheter. Even further, the expandable mechanism on the distal end of these devices could be programmed to be thermally sensitive so that they expand or contract when placed in desired thermal gradients. One such mechanism for 'programming' materials like this is known as Shaped Memory Alloys (SMA) or Two Way Shaped Memory Alloys (TWSMA). Another exemplary embodiment of the instant invention is that once the device is placed in its desired location the mechanism (usually near the distal portion of the device) is deployed to 'lock' or 'anchor' it in the desired position.

Another embodiment is the tensioning characteristic of the instant invention. When the device is in or near a desired location of the body, the distal mechanism is deployed so that it anchors or has a tendency not to move. In this configuration, the wire, catheter or other device can be put into tension that will allow the passage of another device over or with the inner support wire. Even further and discussed heretofore, the instant invention can be 'detached' from the support wire and act as a tubular channel occluder.

This anchoring mechanism may or may not be used with the other embodiments. Further, the flow/contractile force characteristic may or may not be used with the other embodiments. Even further, the tensioning characteristic may or may not be used with the other embodiments. Last, the occluder may be used independently of the other three. In other words, although the distal mechanism that is used for all four embodiments may be similar to one another, the separate four embodiments may be used alone or in combination with the other embodiments.

Referring now to the figures, the four embodiments of the instant invention are illustrated.

Figure 1:
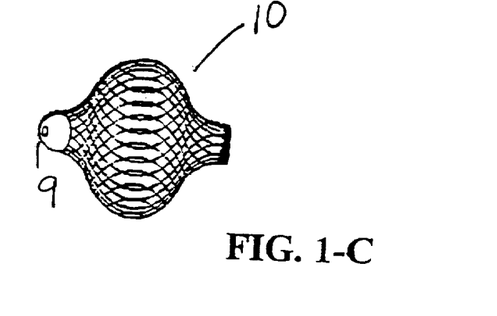
FIG. 1 is a schematic illustration of a guide wire or catheter constructed in accordance with the principles of the present idea.

Turning now to FIG. 1-A, a preferred embodiment of the instant invention is illustrated using a schematic drawing. The radially compressed, smaller support wire 1 is illustrated. The shaft 2 is a tubular outer shell where the inner wire or tube 3 rests. The inner tube 3 is attached to the distal end of the annular braid 4 at 5. The outer shell 2 may be attached to the annular braid at 6. In the case of the detachable occluder in FIG. 1-C, it may not be attached so that the occluder is set free in the desired location.

Referring now to FIG. 1-B, the inner tube or wire 3 is moved relative to the outer shell 2 as indicated by the arrow 7. This relative motion causes the annular braid 4 to expand radially as shown at 8. The shapes shown in these figures show an ovoid shape, however the shape can vary significantly as described heretofore. Notice that there is a through lumen illustrated inside the inner tube 3 and is further indicated at the distal tip of the assembly by 9. This may or may not be required depending on the application.

Turning now to FIG. 1-C, the preferred embodiment of the instant invention as an occluder 10 is illustrated in the schematic.

Figure 2:
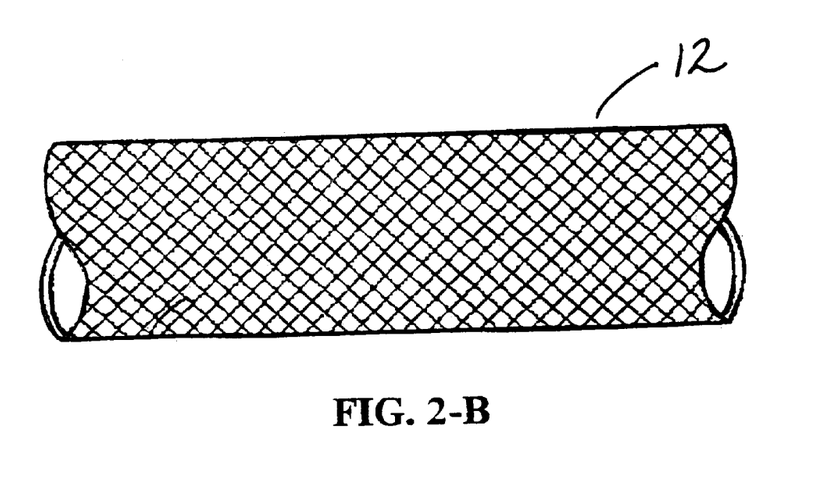
FIG. 2 is a schematic illustration of the annular or tubular braid used in the instant invention.

Referring now to FIGS. 2-A and 2-B, a schematic view of the annular or tubular braid is illustrated. FIG. 2-A illustrates the annular braid in its relaxed, smaller or compressed state 11. FIG. 2-B illustrates the annular braid in its expanded state 12. The expansion is achieved by putting the braid into a compressive mode and changing the overall length of the braid. This can also be accomplished with self expanding of the braid by programming it with thermal treatments or using SMA (Shaped Memory Alloys) or by using a thermal change to change the shape of the device with a technique known as TWSMA (Two Way Shape Memory Alloy).

Figure 3:
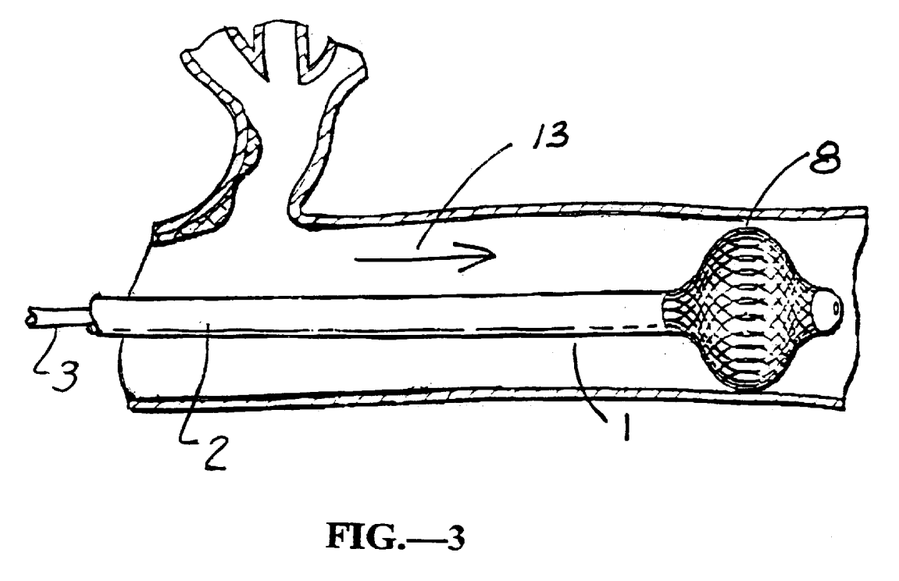
FIG. 3 is a schematic illustration of the expanded braided 'umbrella' mechanism in place in a tubular channel of the body where the expanding element is used as an occluder, anchor, flow director or tensioner.
Figure 3A:
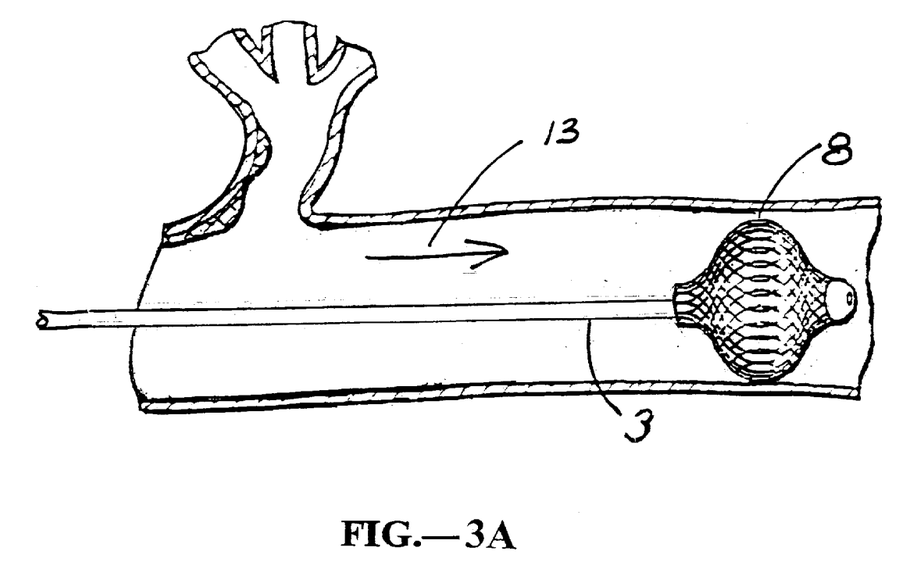

Turning now to FIG. 3, a preferred embodiment is illustrated in a schematic view. This is the expanded device 1 in place in a tubular channel of the body. This figure shows the instant invention as anchor and subsequent tensioner if so desired for the particular application. Further, it could be the preferred embodiment of a flow directed guide wire or device if there is flow in the tubular channel as indicated by the arrow 13. The mechanisms of the preferred embodiment are shown here in FIGS. 3 & 4 inside a tubular channel. However, the preferred embodiment of the instant invention could be used for other anchoring as heretofore disclosed. This anchor could be used for closing percutaneous punctures in the femoral artery for example as well. This is a ubiquitous problem. By deploying the anchor on the inside of the puncture of the vessel (artery or vein), the puncture wound would seal faster. Further dehydrated collagen could be used to aid in this procedure. Even further, this anchor or occluder could be fabricated with bio-resorbable materials as required for the particular application.

Figure 4:
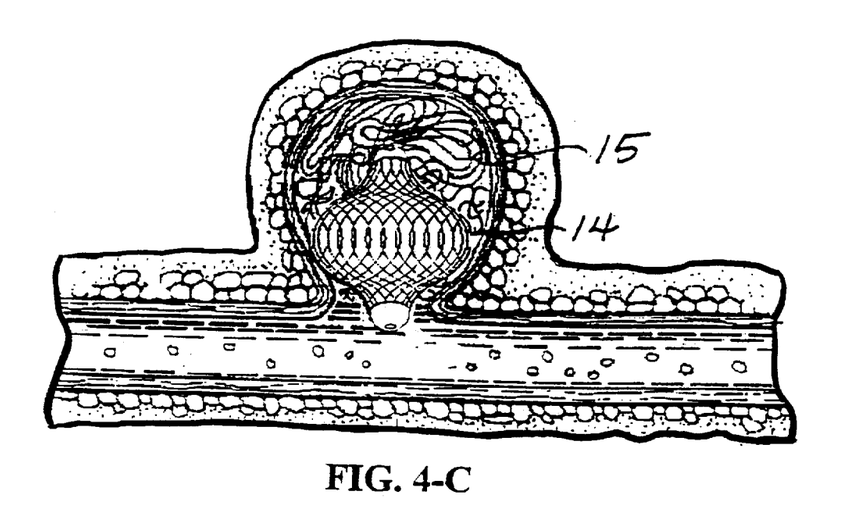
FIG. 4 illustrates the instant invention as it is being used as a detachable occluder.

Turning now to FIG. 4-A, a schematic illustration shows the occluder 14 in place in the vessel. This is accomplished by removing the support wire (inner wire or tube 3 and outer shell 2) as described heretofore. FIG. 4-B shows the instant invention 1 in its smaller condition as it is being passed into a vessel with an aneurysm 15. FIG. 4-C illustrates the occluder 14 in position in the aneurysm thus providing a novel therapy to this dangerous disease.

In any of these instances, the 'desired' location of the device is usually determined using Image Intensification (Fluoroscopy, Ultrasound Imaging, MRI, etc.). Further, the location could be monitored using cameras or other visualization techniques.

The Tubular Braid Elements

The apparatus of the instant invention includes an elongate tube; an elongate mandril inside the tube and an expandable tubular braid. The elongate mandril extends from the proximal end of the device to the distal end. The elongate tube usually extends from close to the proximal end of the device to close to the distal end. The distal end of the tubular braid is bonded to the distal end of the inner elongate mandril. The mandril may extend beyond the tubular braid. The proximal end of the tubular braid is bonded to the distal end of the elongate tube.

The braid may be open, but may be laminated or covered with a coating of elastic, generally inelastic, plastic or plastically deformable material, such as silicone rubber, latex, polyethylene, thermoplastic elastomers (such as C-Flex, commercially available from Consolidated Polymer Technology), polyurethane and the like. The assembly of tube, mandril and braid is introduced percutaneously in its radially compressed state. In this state, the outside diameter of the braid is close to the outside diameter of the elongate tube. This diameter is in the range of 10 to 500 mils, and usually 25 to 250 mils (i.e. thousandth of an inch). After insertion, moving the mandril proximally with respect to the tube expands the tubular braid.

The tubular braid is preferably formed as a mesh of individual non-elastic filaments (called "yarns" in the braiding industry). However, it can have some elastic filaments interwoven to create certain characteristics. The non-elastic yarns can be materials such as polyester, PET, polypropylene, polyamide fiber (Kevlar, DuPont), composite filament wound polymer, extruded polymer tubing (such as Nylon II or Ultem, commercially available from General Electric), stainless steel, Nickel Titanium (Nitinol), or the like so that axial shortening causes radial expansion of the braid. These materials have sufficient strength so that the expanding element will retain its expanded condition in the lumen of the body while removing the matter therefrom. Further, all expandable mechanisms described heretofore, can be manufactured using shape memory materials so that they are self expanding or even expandable when certain temperatures or thermal energies are delivered to the mechanisms. Such material characteristics can be accomplished with different programming methods such as, but not limited to Two Way Shape Memory (TWSM) alloys.

The braid may be of conventional construction, comprising round filaments, flat or ribbon filaments, square filaments, or the like. Non-round filaments may be advantageous to decrease the axial force required for expansion to create a preferred surface area configuration or to decrease the wall thickness of the tubular braid. The filament width or diameter will typically be from about 0.5 to 50 mils, usually being from about 5 to 20 mils. Suitable braids are commercially available from a variety of commercial suppliers.

The tubular braids are typically formed by a "Maypole" dance of yarn carriers. The braid consists of two systems of yarns alternately passing over and under each other causing a zigzag pattern on the surface. One system of yarns moves helically clockwise with respect to the fabric axis while the other moves helically counter-clockwise. The resulting fabric is a tubular braid. Common applications of tubular braids are lacings, electrical cable covers (i.e. insulation and shielding), "Chinese hand-cuffs" and reinforcements for composites. To form a balanced, torque-free fabric (tubular braid), the structure must contain the same number of yarns in each helical direction. The tubular braid may also be pressed flat to form a double thickness fabric strip. The braid weave used in the tubular braid of the present invention will preferably be of the construction known as "two dimensional, tubular, diamond braid" that has a 1/1 intersection pattern of the yarns which is referred to as the "intersection repeat". Alternatively, a Regular braid with a 2/2 intersection repeat and a Hercules braid with an intersection repeat of 3/3 may be used. In all instances, the helix angle (that being the angle between the axis of the tubular braid and the yarn) will increase as the braid is expanded. Even further, Longitudinal Lay-Ins can be added within the braid yarns and parallel to the axis to aid with stability, improve tensile and compressive properties and modulus of the fabric. When these longitudinal "Lay-In" yarns are elastic in nature, the tubular braid is known as an elastic braid. When the longitudinal yarns are stiff, the fabric is called a rigid braid. Biaxially braided fabrics such as those of the present invention are not dimensionally stable. This is why the braid can be placed into an expanded state from a relaxed state (in the case of putting it into the compressive mode). Alternatively this could be a decreased/reduced (braid diameter decreases) state when put into tension from the relaxed state. When put into tension (or compression for that matter) the braid eventually reaches a state wherein the diameter will decrease no more. This is called the "Jammed State". On a stress strain curve, this corresponds to increase modulus. Much of the engineering analyses concerning braids are calculated using the "Jammed State" of the structure/braid. These calculations help one skilled in the art to design a braid with particular desired characteristics. Further, material characteristics are tensile strength, stiffness and Young's modulus. In most instances, varying the material characteristics will vary the force with which the expanded condition of the tubular can exert radially. Even further, the friction between the individual yarns has an effect on the force required to compress and un-compress the tubular braid. For the present invention, friction should be relatively low for a chosen yarn so that the user will have little trouble deploying the engaging element. This is particularly important when the engaging element is located a significant distance from the user. Such is the case when the percutaneous entry is the groin (Femoral Artery for vascular interventions) and the point of engaging the engaging element is some distance away (i.e. the Carotid Artery in the neck). Similarly, this is true for long distances that are not vascular or percutaneous applications.

An exemplary device has the following characteristics:
Working Length
30–500 cm
Working Diameter
The guide wire, catheter, endoscope or other device of the present idea has an outer diameter that ranges from 0.006" to 0.315", but can extend to smaller and larger sizes as technology and procedures require.
Physical Configuration
The device of the present idea will have a predetermined shaped (probably circular in diameter of 6–10") coiled in the package, "as supplied". Alternatively the product/device may be supplied straight but may have a shape at the distal end. The distal end may be tapered to a smaller distal diameter. This tapering may occur in the distal 6–12" of the device, but could occur over a greater length and there may be more than one taper along its length. Optionally, the device may have a shaped tip or a tip that may be malleable so that the user prior to introduction may shape it.

The device of the instant invention may have conventional lubricious coatings to enhance introduction into the target body lumen, e.g. hyaluronic or other equivalent coatings. Further, the user, prior to insertion may apply a lubricious coating. This may be extremely useful in the case of a reusable device (like an endoscope). As an advantage of the present idea, the device will be less difficult to feed it to the desired location in the body. Further difficulty will be greatly decreased for placement of other devices over or with the inner device. Even further, the instant invention will be less difficult to remain in the target location. This decreased difficulty will decrease cost due to time in the Operating Room (Operating Rooms costs are estimated in excess of $90 dollars per minute in the U.S.) or other environment. Additionally, the decrease in difficulty will aid in patient care and the potential in deleterious effects due to the inability to place the device in the appropriate position in the patient and keep it there or to place other devices with the present idea.

An exemplary device having an expanding 'umbrella' mechanism located on its distal tip is illustrated in the figures. This mechanism may be at the tip or somewhere else in the distal portion of the device. Additionally, this mechanism may be any of a number of mechanisms that will help aid in moving the device using the physiological environment of the body. Alternatively, this distal mechanism may be used for anchoring, flow direction, tensioning or occluding. In this particular embodiment, a distal portion of the device may not coiled and will thus retain the malleable or resilient characteristics typical of conventional devices.

Although the foregoing idea has been described in some detail by way of illustration and example, for purposes of clarity of understanding, it will be obvious that certain changes and modifications may be practiced within the scope of the appended claims.

What is claimed is:

1. An improved medical device for use in the body, comprising:
   a support element insertable into the body, said support element comprising a shaft and an elongate member, said support element having a distal end;
   an expandable element supported on said distal end of said support element, said expandable element movable from a radially compressed state, for insertion of said expandable element into the body, to a radially expanded state using the shaft and the elongate member to axially compress and thereby radially expand said expandable element;
   said expandable element comprising structural members which define openings therebetween;
   said expandable element having a radial dimension in the radially expanded state which is at least four times larger than when in the radially compressed state; and
   said expandable element comprising an expandable polymer at least substantially filling said openings to create a substantially non-porous expandable element when in the radially expanded state.

2. The device of claim 1 wherein the polymer comprises a film layer.

3. The device of claim 2 wherein the expandable element is an annular braided expandable element and the film layer contacts the annular braided expandable element.

4. The device of claim 3 wherein the film layer covers the annular braided expandable element.

5. The device of claim 1 wherein said expandable element is a multi-wing malecot expandable element and said film comprises an annular elastomeric film around said wings.

6. The device of claim 1 wherein said shaft and expandable element define a longitudinally-extending through lumen to permit an elongate element to pass along the shaft and completely through the expandable element.

7. The device of claim 1 wherein said expandable element is an anchoring element for a supplemental medical device.

8. The device of claim 1 wherein said expandable element is a tubular channel occlusion element.

9. The device of claim 1 wherein said expandable element is a flow-directed, releasable expandable element.

10. The device of claim 1 wherein said expandable element is an annular braided expandable element having individual yarns sufficiently flexible to be moved between said states and sufficiently stiff to substantially hold said expanded state when in a targeted area within a body.

11. An improved medical device for use in the body, comprising:
    a support element insertable into the body, said support element comprising a shaft and an elongate member, said support element having a distal end;
    an expandable element supported on said distal end of said support element, said expandable element movable from a radially compressed state, for insertion of said expandable element into the body, to a radially expanded state using the shaft and the elongate member to axially compress and thereby radially expand said expandable element;
    said expandable element comprising structural members which define openings therebetween;
    said expandable element comprising a expandable polymer at least substantially filling said openings to create a substantially non-porous expandable element when in the radially expanded state; and
    the expandable element supported on said distal end of said support element, said expandable element movable from a radially expanded state, to a radially compressed state for insertion of said expandable element into the body using the shaft and the elongate member to axially extend and thereby radially compress said expandable element.

12. The device of claim 1 or 11 wherein the expandable element is releasable from both the elongate member and the shaft.

13. The device of claim 1 or 11 wherein the polymer comprises thin strands of expandable polymer.

14. The device of claim 13 wherein the expandable element is an annular braided expandable element and the expandable polymer contacts the annular braided expandable element.

15. The device of claim 14 wherein the expandable polymer covers the annular braided expandable element.

16. The device of claim 14 wherein the polymer interweaves the annular braided expandable element.

17. The device of claim 1 or 11 wherein said expandable element is sized so to contact a wall of a passageway in which it is inserted.

18. The device of claim 1 or 11 wherein the expandable element is bioabsorbable.

19. The device of claim 1 or 11 wherein said expandable element comprises an annular braided expandable element.

20. The device of claim 1 or 11 wherein said expandable element comprises a multi-wing malecot expandable element.

21. An improved medical device for use in the body, comprising:
    a support element insertable into the body, said support element comprising a shaft and an elongate member, said support element having a distal end;
    an expandable element supported on said distal end of said support element, said expandable element movable from a radially compressed state, for insertion of said expandable element into the body, to a radially expanded state using the shaft and the elongate member to axially compress and thereby radially expand said expandable element;
    said expandable element comprising an annular braided expandable element comprising structural members which define openings therebetween;
    said expandable element comprising a film at least substantially filling said openings to create a substantially non-porous expandable element; and the expandable element being releasable from both the elongate member and the shaft.

22. The device of claim 21 wherein the expandable element is releasable from the elongate member and the shaft when in the radially expanded state.

23. The device of claim 22 wherein the expandable element is bioabsorbable.

24. A method for placing an expandable element within a hollow body structure within a body through which fluid flows, comprising:

selecting a medical device comprising a support member and an expandable element at the distal end of the member, the expandable element comprising structural members which define openings therebetween and a film at least substantially filling said openings;

the selecting step to comprising choosing a flow-directed expandable element as the expandable element;

positioning the flow-directed expandable element at a chosen location within a hollow body structure of a body;

expanding the flow-directed expandable element from a radially compressed state to a radially expanded state; and releasing the flow-directed expandable element from the support member thereby permitting the flow-directed expandable element to be directed by fluid flowing through said hollow body structure.

25. An improved medical device for use in the body, comprising:

a support element insertable into the body, said support element comprising a shaft and an elongate member, said support element having a distal end;

an axially-compressible, radially-expandable expandable element supported on said distal end of said support element, said expandable element movable from a radially compressed state, for insertion of said expandable element into the body, away from a relaxed, radially-contracted state to a radially expanded state using the shaft and the elongate member to axially compress and thereby radially expand said expandable element;

said expandable element comprising structural members which define openings therebetween;

said expandable element having a radial dimension in the radially expanded state which is at least four times larger than when in the radially compressed state; and said expandable element comprising a stretchable film at least substantially filling said openings to create a substantially non-porous expandable element when in the radially expanded state.

26. The device of claim 25 wherein the expandable element is an annular braided expandable element and the film comprises a film layer which contacts the annular braided expandable element.

27. The device of claim 25 wherein the expandable element is an annular braided expandable element and the film comprises an expandable polymer which contacts the annular braided expandable element.

28. An improved medical device for use in the body, comprising:

a support element insertable into the body, said support element comprising a shaft and an elongate member, said support element having a distal end;

an axially-compressible, radially-expandable expandable element supported on said distal end of said support element, said expandable element movable from a radially compressed state, for insertion of said expandable element into the body, away from a relaxed, radially-contracted state to a radially expanded state using the shaft and the elongate member to axially compress and thereby radially expand said expandable element;

said expandable element comprising structural members which define openings therebetween;

said expandable element having a radial dimension in the radially expanded state which is at least four times larger than when in the radially compressed state; and said expandable element comprising an expandable polymer at least substantially filling said openings to create a substantially non-porous expandable element when in the radially expanded state.

29. The device of claim 25 or 28 wherein the expandable element is releasable from both the elongate member and the shaft.

30. A method for placing an expandable element within a body comprising:

selecting a medical device comprising a support member and an axially-compressible, radially-expandable expandable element at the distal end of the support member, the expandable element comprising structural members which define openings therebetween and a film at least substantially filling said openings;

positioning the expandable element at a chosen location within a body;

axially compressing the expandable element away from a relaxed, radially-contracted state thereby expanding the expandable element from a radially compressed state to a radially expanded state;

releasing the expandable element from the support member; and removing the support member from the body with the expandable element in the expanded state within the body.

31. A method for placing an expandable element within a body comprising:

selecting a medical device comprising a support member and an axially-compressible, radially-expandable expandable element at the distal end of the support member, the expandable element comprising structural members which define openings therebetween and an expandable polymer at least substantially filling said openings;

positioning the expandable element at a chosen location within a body;

axially compressing the expandable element away from a relaxed, radially-contracted state thereby expanding the expandable element from a radially compressed state to a radially expanded state;

releasing the expandable element from the support member; and removing the support member from the body with the expandable element in the expanded state within the body.

32. An improved medical device for use in the body, comprising:

a support element insertable into the body, said support element comprising a shaft and an elongate member, said support element having a distal end;

an axially-compressible, radially-expandable expandable element supported on said distal end of said support element, said expandable element movable from a radially compressed state, for insertion of said expandable element into the body, away from a relaxed, radially-contracted state to a radially expanded state using the shaft and the elongate member to axially compress and thereby radially expand said expandable element;

said expandable element comprising an annular braided expandable element comprising structural members which define openings therebetween;

said expandable element comprising a film at least substantially filling said openings to create a substantially non-porous expandable element; and the expandable element being releasable from both the elongate member and the shaft.

33. A method for placing an expandable element within a hollow body structure within a body through which fluid flows, comprising:

selecting a medical device comprising a support member and an axially-compressible, radially-expandable expandable element at the distal end of the support member, the expandable element comprising structural members which define openings therebetween and a film at least substantially filling said openings;

the selecting step comprising choosing a flow-directed expandable element as the expandable element;

positioning the flow-directed expandable element at a chosen location within a hollow body structure of a body;

expanding the flow-directed expandable element away from a relaxed, radially contracted state by expanding the expandable element from a radially compressed state to a radially expanded state; and releasing the flow-directed expandable element from the support member thereby permitting the flow-directed expandable element to be directed by fluid flowing through said hollow body structure.

* * * * *